(12) United States Patent
Alaqeel

(10) Patent No.: US 12,426,776 B1
(45) Date of Patent: Sep. 30, 2025

(54) APPARATUS FOR CLEANING A LAPAROSCOPE

(71) Applicant: KING SAUD UNIVERSITY, Riyadh (SA)

(72) Inventor: Amirah Nasser Alaqeel, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/885,258

(22) Filed: Sep. 13, 2024

(51) Int. Cl.
A61B 1/00 (2006.01)
A61B 1/12 (2006.01)
A61B 90/70 (2016.01)

(52) U.S. Cl.
CPC .............. A61B 1/122 (2013.01); A61B 1/125 (2013.01); A61B 90/70 (2016.02); A61B 2090/701 (2016.02)

(58) Field of Classification Search
CPC ......... A61B 1/122; A61B 1/125; A61B 1/121; A61B 1/126; A61B 90/70; A61B 2090/701
USPC .......................................................... 600/157
See application file for complete search history.

(56) References Cited

U.S. PATENT DOCUMENTS

| 5,518,502 A * | 5/1996 | Kaplan | A61B 1/127 600/156 |
| 8,550,988 B2 | 10/2013 | Pribanic | |
| 9,913,576 B2 | 3/2018 | Ray et al. | |
| 10,463,237 B2 | 11/2019 | Saadat et al. | |
| 11,013,399 B1 * | 5/2021 | Idelson | G02B 23/2476 |
| 11,089,952 B2 * | 8/2021 | Irion | A61B 1/05 |
| 2002/0065450 A1 * | 5/2002 | Ogawa | A61B 1/126 600/157 |
| 2009/0240111 A1 * | 9/2009 | Kessler | A61B 1/126 600/179 |
| 2012/0101337 A1 * | 4/2012 | Clark | A61B 1/00091 600/157 |
| 2012/0101338 A1 * | 4/2012 | O'Prey | A61B 1/126 600/157 |
| 2013/0211197 A1 | 8/2013 | Kano et al. | |

(Continued)

FOREIGN PATENT DOCUMENTS

KR 2011-0130268 A 12/2011
KR 109549617 A 4/2019

Primary Examiner — Anh Tuan T Nguyen
Assistant Examiner — James Edward Boice
(74) Attorney, Agent, or Firm — Nath, Goldberg & Meyer; Joshua B. Goldberg

(57) ABSTRACT

An apparatus for cleaning a laparoscope includes a housing configured to be selectively connected to the laparoscope, a fluid-moving assembly connected to the housing, a wiping assembly connected to the housing, and a trigger movably connected to the housing. The housing may include first transparent portion thereof covering a camera of the laparoscope. The fluid-moving assembly is configured to receive a cleaning fluid and to direct the fluid toward the first transparent portion of the housing. The wiping assembly is configured to wipe the first transparent portion of the housing. The trigger is configured to be selectively moved between a first position and a second position relative to the housing to cause the fluid-moving assembly to spray the fluid toward the first transparent portion of the housing and to cause the wiping blade to wipe the first transparent portion of the housing.

8 Claims, 6 Drawing Sheets

(56) References Cited

U.S. PATENT DOCUMENTS

| | | | |
|---|---|---|---|
| 2015/0201826 A1* | 7/2015 | Hsu | A61B 1/018 600/121 |
| 2016/0113484 A1 | 4/2016 | Nakaguchi | |
| 2018/0116496 A1* | 5/2018 | Arcot | H02S 40/36 |
| 2020/0405144 A1 | 12/2020 | Fowler et al. | |
| 2024/0024904 A1* | 1/2024 | Youdovin | B05B 11/1057 |

* cited by examiner

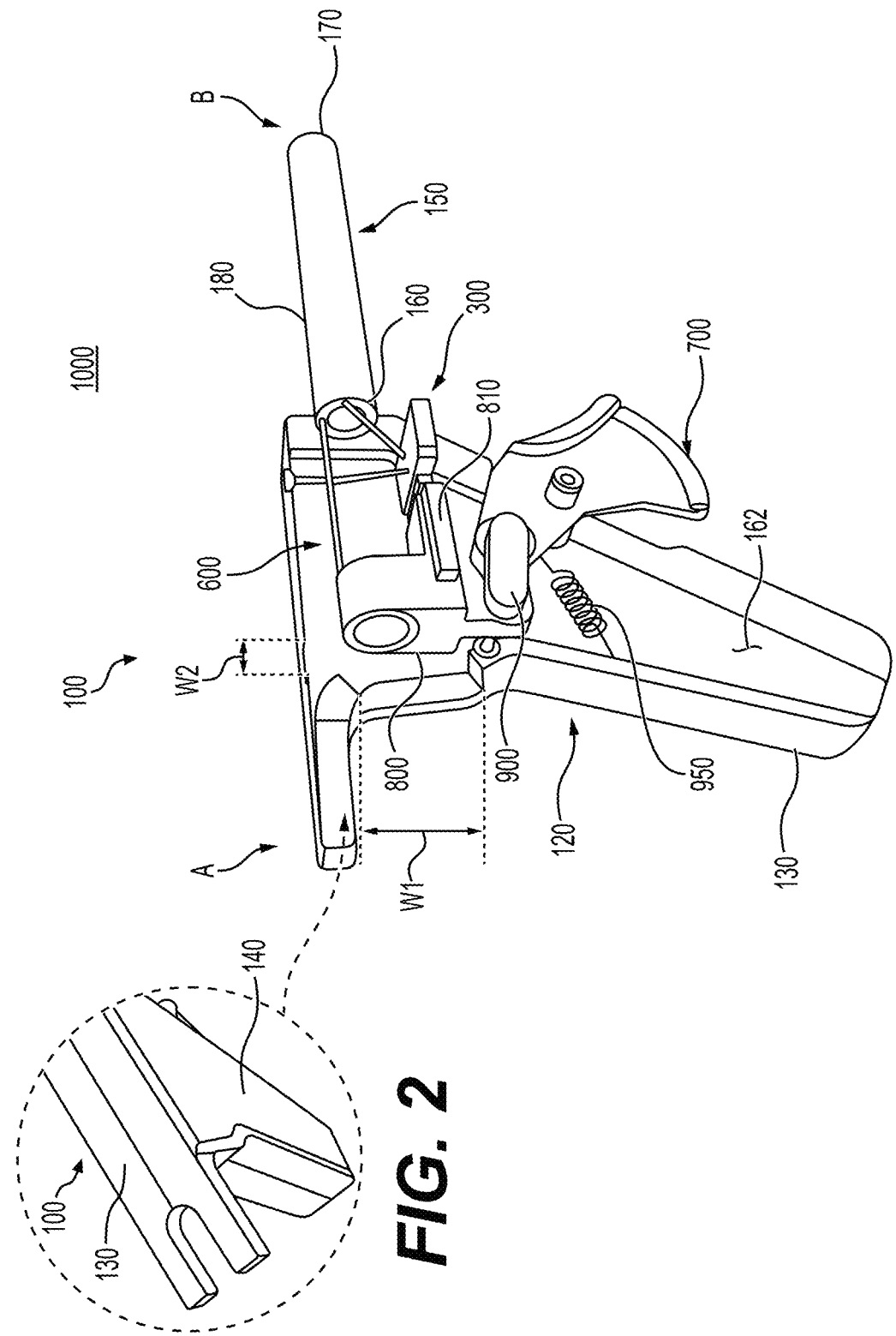

APPARATUS FOR CLEANING A LAPAROSCOPE

TECHNICAL FIELD

The present disclosure relates to laparoscopy, and more particularly, to an apparatus for cleaning a laparoscope during a surgical procedure by directing a saline solution toward the laparoscope's camera and wiping the saline solution off the camera with a wiping blade.

DISCUSSION OF THE RELATED ART

Laparoscopy is an operation performed in the abdomen or pelvis by using small incisions with the aid of a camera included in a device called a laparoscope. Laparoscopy is less invasive than traditional abdominal or pelvic surgery because it requires only a small incision in the skin for inserting the laparoscope underneath.

However, the camera lens of the laparoscope tends to become dirty with bodily fluids and/or bodily matter during the surgical procedure. This, in turn, prevents the operating surgeon from seeing the surgical site clearly via a monitor providing a live feed of the laparoscope's camera. As a result, the surgeon or assisting medical staff must periodically retract the laparoscope from the surgical site to clean the camera's lens. The laparoscope is then reinserted in the patient's body through the incision. The procedure of removing the laparoscope from the surgical site, cleaning the laparoscope's camera, and reinserting the laparoscope in the surgical site is disadvantageous because it unnecessarily extends the length of the surgical procedure without providing any benefit.

SUMMARY

The present disclosure relates to an apparatus configured to selectively receive a laparoscope therein. The apparatus of the present disclosure is configured to be connected to a source of a cleaning fluid (e.g., a saline bag). The apparatus of the present disclosure is configured to receive cleaning fluid from the source thereof, to spray (or otherwise wet) the camera of the laparoscope with the cleaning fluid, and to wipe the sprayed/wet camera of the laparoscope with a wiping blade. The spraying and wiping actions are performed to clean the laparoscope's camera. Both spraying and wiping actions can be performed by squeezing a trigger of the apparatus of the present specification.

Moreover, the apparatus of the present disclosure can be used to clean the laparoscope's camera wile the laparoscope is inserted in a patient's body during a laparoscopic procedure. Therefore, the surgeon need not retract the laparoscope from the patient's body to clean its lens during the laparoscopic procedure (the camera becomes dirty during the procedure, thereby reducing the quality of the images obtained from the camera).

The apparatus of the present specification is easy to use because it can be held and operated by using only one hand. That is, one or more of the fingers of the hand that is holding said apparatus can be used to squeeze the trigger for cleaning the lens of the laparoscope's camera. In addition, the ability of the apparatus of the present disclosure to clean a laparoscope's camera while the laparoscope is inserted in a patient's body during a laparoscopic procedure eliminates the need to take the laparoscope out of the patient's body for cleaning, thereby significantly reducing the overall operation time. The reduction of operation time can increase the patient's recovery rate and increase the availability of hospital staff, beds and resources.

BRIEF DESCRIPTION OF THE DRAWINGS

The above and other features of the present disclosure will become more apparent by describing in detail exemplary embodiments thereof in conjunction with the accompanying drawings, in which:

FIG. 1 is a perspective view illustrating a portion of an apparatus for cleaning a laparoscope;

FIG. 2 is a perspective view illustrating a portion "A" of the apparatus of FIG. 1;

DETAILED DESCRIPTION OF THE EMBODIMENTS

Figure 3:
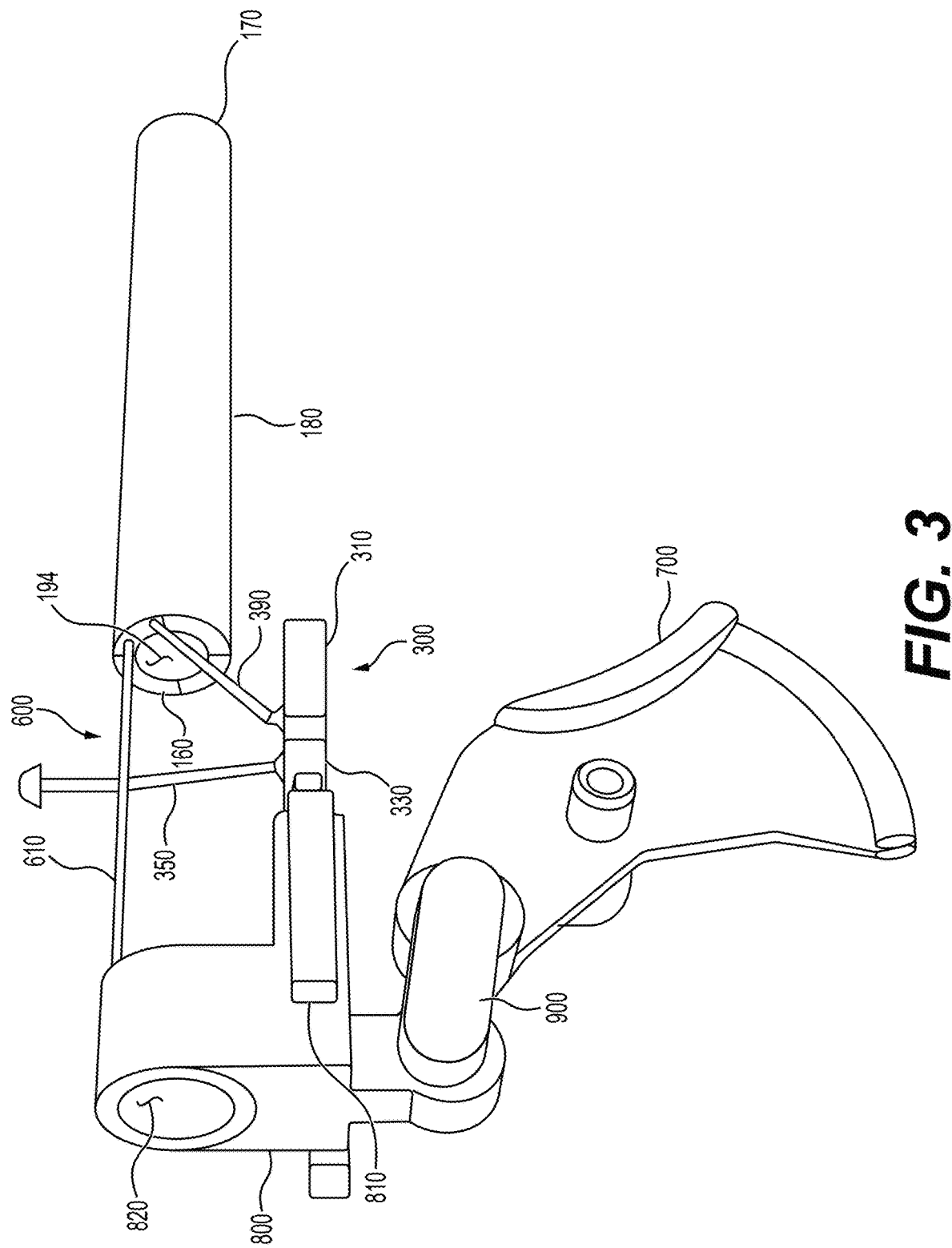
FIG. 3 is a perspective view illustrating a portion of the apparatus of FIG. 1.

Exemplary embodiments of the present disclosure will be described more fully hereinafter with reference to the accompanying drawings. The present disclosure may, however, be embodied in different forms and should not be construed as being limited to the embodiments set forth herein. Like reference numerals may refer to like elements throughout the specification. The sizes and/or proportions of the elements illustrated in the drawings may be exaggerated for clarity.

When an element is referred to as being disposed on another element, intervening elements may be disposed therebetween. In addition, elements, components, parts, etc., not described in detail with respect to a certain figure or embodiment may be assumed to be similar to or the same as corresponding elements, components, parts, etc., described in other parts of the specification.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" may include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

FIGS. 1-7 illustrate an apparatus 1000 for cleaning a laparoscope. For example, a laparoscope can be selectively connected to the apparatus 1000. The apparatus 1000 can be used to clean a camera of the laparoscope during a laparoscopic procedure when a front end of the laparoscope, containing the laparoscope's camera (with the laparoscope being selectively connected to the apparatus 1000), is inserted under a patient's skin. More specifically, the apparatus 1000 can be used to clean the laparoscope's camera without removing the laparoscope's front end from the surgical site (i.e., the cleaning process can be performed with the front end of the laparoscope being inserted under the skin).

Referring to FIGS. 1-7, the apparatus 1000 includes a housing 100, a fluid-moving assembly 300 connected to the housing 100, a wiping assembly 600 connected to the housing 100, and a trigger 700. The trigger 700 is movably connected to the housing 100, operably connected to the fluid-moving assembly 300, and operably connected to the wiping assembly 600.

Figures 4A, 4B:
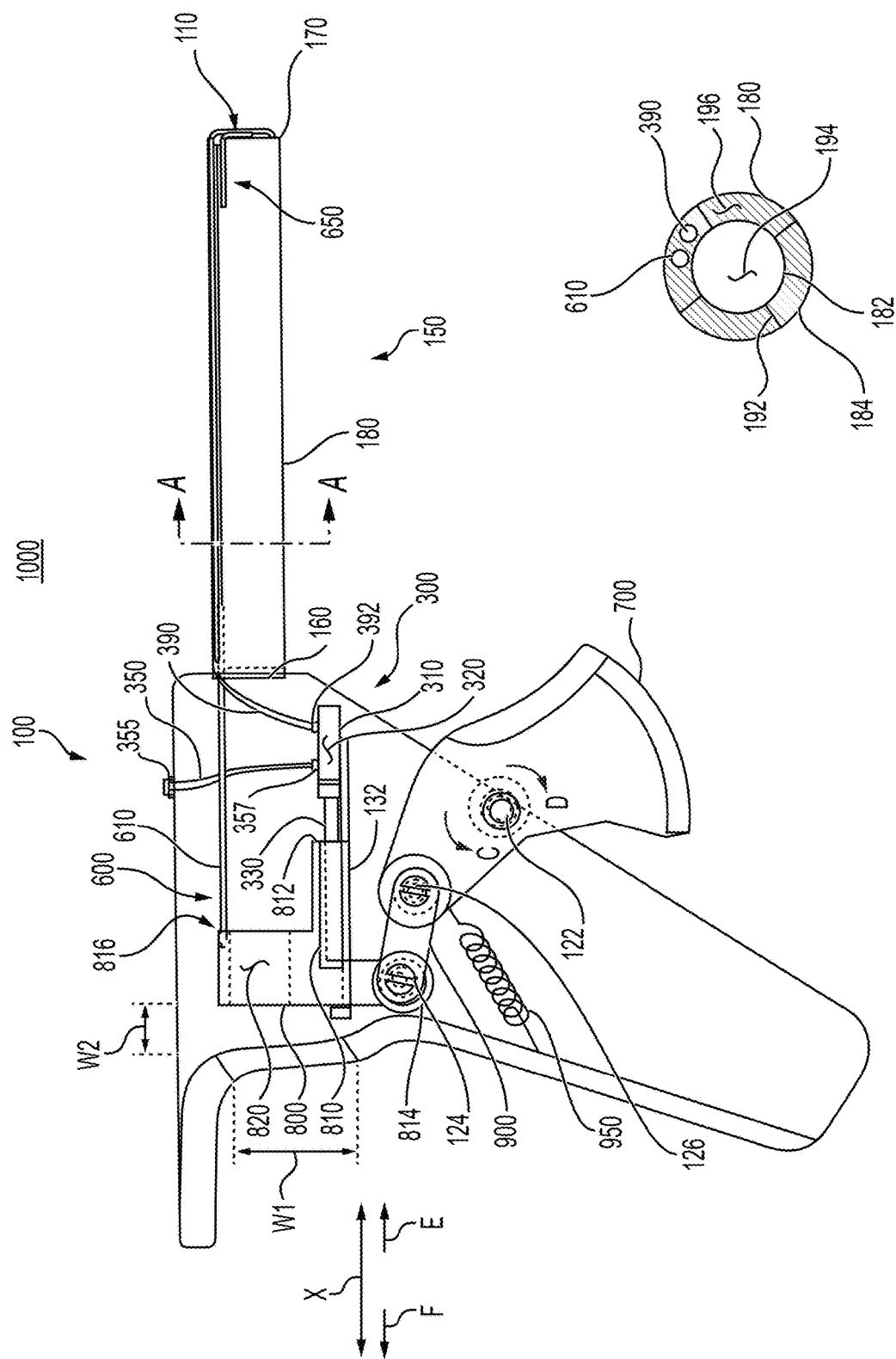
FIG. 4A is a side view illustrating the apparatus of FIG. 1.
FIG. 4B is a cross-sectional view taken along line A-A of FIG. 4A.

In a non-limiting approach, and as illustrated in FIGS. 1, 3 and 4, the apparatus 1000 may include a first connector 800, a linking member 900 for movably connecting the trigger 700 with the fluid-moving assembly 300 and the wiping assembly 600, and an elastic member 950 (e.g., a spring) configured to rotatably bias the trigger 700 in a direction "C", as illustrated in FIG. 4A.

The fluid-moving assembly 300 is configured to receive a fluid therein (e.g., a saline solution, distilled water, and/or other fluids that are safe for coming into contact with the internal tissue and/or organs of a patient during a laparoscopic surgical procedure) and to direct the received fluid toward a predetermined location 110 of the apparatus 1000 (see FIGS. 5 and 6) where the laparoscope's camera is located when the laparoscope is selectively connected to the housing 100. The laparoscope's camera will be referred to as a "camera" hereinafter for brevity purposes.

In a first non-limiting approach, the housing 100 has a transparent protective layer configured to cover the camera when the laparoscope is selectively connected to the apparatus 1000. That is, the transparent protective layer is located on the outside of the camera when the laparoscope is connected to the apparatus 1000, thereby structurally protecting the camera's lens and preventing the camera's lens from coming into direct contact with the patient's bodily fluids, tissue and/or organs during the laparoscopic procedure. In this approach, the "predetermined location" 110 is the location of the transparent protective layer of the housing 100.

In a second non-limiting approach, the housing 100 has a through opening configured to expose the camera to an exterior of the housing 100 when the laparoscope is selectively connected to the apparatus 1000. This configuration enables the camera to come into direct contact with the bodily fluids, tissue and/or organs of the patient during the laparoscopic procedure. In this non-limiting approach, the "predetermined location" 110 is the location of the camera's lens when the laparoscope is selectively connected to the apparatus 1000.

Therefore, and regardless of which approach is taken in constructing the housing 100, the apparatus 1000 is configured to clean the lens itself, or to clean the transparent protective layer covering the camera lens, as the case may be.

Referring to FIGS. 1-2, the housing 100 may include a first housing component 120 and a second elongated housing component 150 extending from the first housing component 120.

The first housing component 120 defines a handle portion of the apparatus 1000. The first housing component 120 may include a first handle portion 130 (see FIGS. 1 and 2) and a second handle portion 140 (see FIG. 2). The first and second handle portions 130, 140 may be mirror opposites of one another, and may be selectively connectable to one another. Alternatively, the first and second handle portions 130, 140 may be formed together as a single component.

The first and second handle portions 130, 140 and the second elongated housing component 150 may be made of a metal, an elastomeric material, etc., or a combination thereof. The metal and the elastomeric material may be, for example, materials capable of repeatedly undergoing a sterilization process without sustaining structural damage as a result thereof (since the apparatus 1000 is intended to come in contact with human body parts during a surgical procedure), and without reacting with human body parts.

The metal may be, for example, stainless steel, (e.g., surgical grade stainless steel), titanium, chromium, nickel, etc., or alloys thereof. The elastomeric material may be, for example, polycarbonate, polyvinyl chloride (PVC), acrylic, nylon, etc., or blends thereof.

Figure 6:
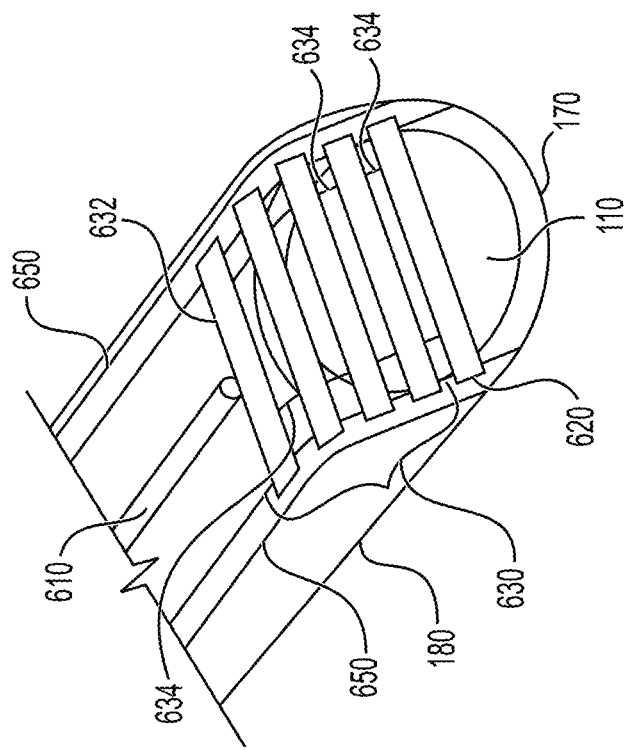
FIG. 6 is a perspective view illustrating the portion "B" of the apparatus of FIG. 1 in a second state.
Figure 5:
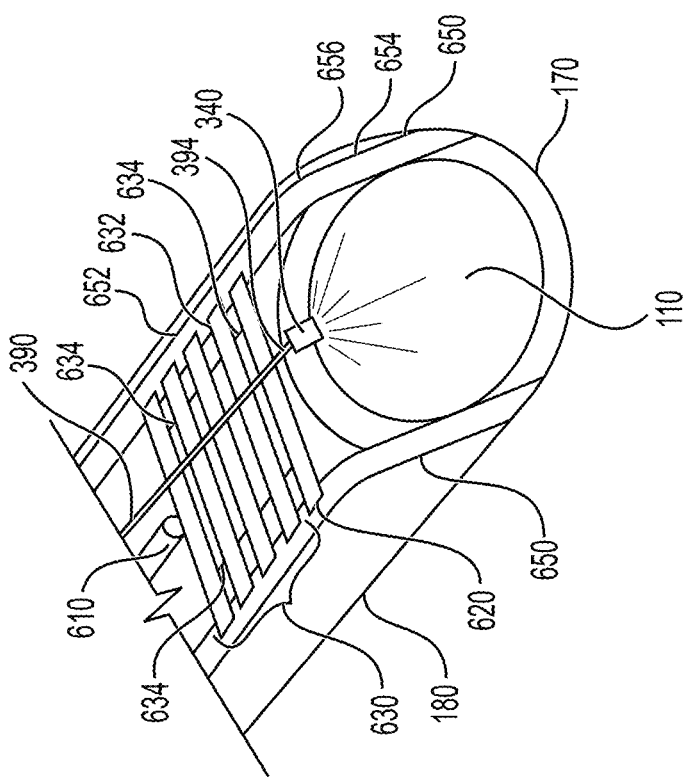
FIG. 5 is a perspective view illustrating a portion "B" of the apparatus of FIG. 1 in a first state.

The second elongated housing component 150 includes the predetermined location 110 (see FIGS. 5 and 6). When the predetermined location 110 is a transparent protective layer, the transparent protective layer may be made of a transparent material that exhibits a strong resistance to shattering, that can be repeatedly sterilized without experiencing significant structural degradation, and that is non-reactive with human body parts. For example, the transparent protective layer can be made of shatter resistant glass, transparent acrylic material, transparent polycarbonate material, etc.

The first and second handle portions 130, 140 define an exterior of the first housing component 120 and an interior space 162 (see FIG. 1) of the first housing component 120.

As illustrated in FIG. 1, the first connector 800, the linking member 900, the elastic member 950, at least one component of the fluid-moving assembly 300 and at least one component of the wiping assembly 600 may be housed in the interior space 162.

Referring to FIGS. 3 and 4A, the second elongated housing component 150 may include a first end 160 connected to the first handle portion 130 and/or the second handle portion 140, a second end 170 opposite to the first end 160, and an elongated body 180 extending between the first and second ends 160, 170. The elongated body 180 may be referred to simply as the "body" 180 for brevity purposes.

Referring to FIG. 3, the body 180 may include a first tubular component 182 extending between the first and second ends 160, 170, and a second tubular component 184 extending between the first and second ends 160, 170. The second tubular component 184 may be spaced from the first tubular component 182 via webs 192. See FIG. 4B. A "web" 192 is a spacer material, for example, a flat bar as illustrated in FIG. 4B.

Referring to FIG. 4B, the first tubular component 182 defines an interior space 194 in which a first portion (e.g., a front portion) of a laparoscope can be received when coupling the laparoscope to the apparatus 1000. Referring to FIGS. 3 and 4A, the first connector 800 may include an interior space 820 in which a second portion (e.g., a rear portion) of the laparoscope can be received when coupling the laparoscope to the apparatus 1000.

As illustrated in FIG. 4B, a second conduit 390 of the fluid-moving assembly 300 and a shaft 610 of the wiping assembly 600 can be housed in and extend along one of a plurality of spaces 196 formed between the first and second tubular components 182, 184 and the webs 192 of the body 180 of the second elongated housing component 150.

Referring to FIG. 4A, the fluid-moving assembly 300 may include a fluid reservoir 310, the fluid reservoir 310 having an interior chamber 320, a first conduit 350 in fluid communication with the interior chamber 320 of the fluid reservoir 310, the second conduit 390 in fluid communication with the interior chamber 320 of the fluid reservoir 310, a plunger 330 movably engaged with the interior chamber 320 of the fluid reservoir 310, and a nozzle 340 (see FIG. 5) connected to an outflow end of the second conduit 390.

Referring to FIG. 4A, the first conduit 350 is configured to convey the fluid from an inflow end 355 thereof to the interior chamber 320, to which it is connected via an outflow end 357 thereof. The first conduit 350 is configured to be fluidly connected to an exterior fluid source, which may be, for example, a saline bag, a saline container, or a container of other fluid as taught by this specification. The first fluid conduit 350 may include a one-way valve to prevent backflow of the fluid (i.e., flow of the fluid toward the inflow end 355).

The plunger 330 is inserted is inserted in the interior chamber 320, and is movable within the interior chamber 320 between a first position thereof, in which the plunger 330 extends inside of the interior chamber 320 of the fluid reservoir 310 by a first distance, and a second position thereof, in which the plunger 330 extends inside of the interior chamber 320 by a second distance, greater than the first distance. That is, the plunger is inserted deeper into the interior chamber 320 when moved from the first position thereof to the second position thereof.

The movement of the plunger 330 from the first position thereof to the second position thereof is configured to push the fluid located in the interior chamber 320 toward the predetermined location 110 via the second conduit 390 and the nozzle 340.

Referring to FIG. 4A, the second conduit 390 is configured to receive the fluid pushed out of the interior chamber 320 (as a result of the plunger 330 being moved from the first position thereof to the second position thereof) via an inflow end 392 of the second conduit 390. The second conduit 390 is configured to convey the received fluid to an outflow end 394 of the second conduit 390 (see FIG. 5).

The nozzle 340 may be connected to the outflow end 394 of the second conduit 390. The nozzle 340 is configured to direct the fluid received from the second conduit 390 toward the predetermined location 110 such that the fluid can come in contact with the camera lens or the transparent protective layer over the camera lens when the laparoscope is connected to the apparatus 1000 (i.e., to wet the predetermined location 110 with the fluid). The fluid ejected from the nozzle 340 can be used to clean the camera lens or the transparent protective layer covering the camera lens.

The nozzle 340 can be omitted in an embodiment. When the nozzle 340 is omitted, the outflow end 394 of the second conduit 390 can be configured (e.g., bent to shape, etc.) to direct the ejected fluid toward the camera lens or toward the transparent protective layer over the camera lens.

Therefore, the camera lens or the transparent protective layer covering the camera lens can be wetted with the fluid when the plunger 330 is pushed into the interior chamber 320 (i.e., when the plunger 330 is moved from the first position thereof to the second position thereof).

The interior chamber 320 of the fluid reservoir 310 can be refilled with fluid via the first conduit 350 when the plunger 330 is retracted from the second position thereof to the first position thereof. After the refilling process, the plunger 330 can be moved again from the first position thereof to the second position thereof to wet the camera lens or the transparent protective layer over the camera lens with the fluid again. The process of refilling the interior chamber 320 of the fluid reservoir 310 with the fluid and wetting the camera lens or the transparent protective layer over the camera lens can be performed repeatedly by moving the plunger 330 between the first and second positions thereof as taught by this specification.

The mechanism for moving the plunger 330 between the first and second positions thereof will be described below in detail with reference to the trigger 700, the linking member 900 and the first connector 800.

As illustrated in FIG. 4A, the trigger 700 may be rotatably coupled to the first and/or second handle portions 130, 140 via a first pin 122. The first and/or second handle portions 130, 140 may each include an elongated guide member 132 extending along a first axis X. The first connector 800 may be a block of material configured to be moved in opposite directions "E" and "F", which run parallel to the first axis X (see FIG. 4A). The first connector 800 is movably connected to the elongated guide member(s) 132 such that the first connector 800 can be moved along the length of the elongated guide member(s) 132 in opposite directions "E" and "F" (e.g., back and forth).

Different physical configurations can be used to movably or slidably connect the first connector 800 to the elongated guide member(s) 132. For example, the elongated guide member 132 of each one of the first and/or second handle portion(s) 130, 140, can be a protrusion of said handle portions. The first connector 800 may include a matching protrusion 810 on either side thereof (see FIGS. 1 and 4A) configured to slide back and forth against the length of the elongated guide member 132 of the first and/or second handle portion(s) 130, 140. In a non-limiting example, the first and/or second handle portion(s) 130, 140 may each include a pair of parallel elongated guide member 132. Said pair of parallel elongated guide members 132 can be movably connected to a matching protrusion 810 of the first connector 800 to ensure that the first connector 800 can be moved in the directions "E" and "F" only.

As illustrated in FIG. 4A, a first portion 812 of the first connector 800 is connected to the plunger 330.

Referring to FIG. 4A, the linking member 900 is rotatably connected to the first connector 800 and the trigger 700. For example, and as illustrated in FIG. 4A, a first end of the linking member 900 can be rotatably connected to a second portion 814 of the first connector 800 via a second pin 124, and a second end of the linking member 900 can be connected to the trigger 700 via a third pin 126.

A user can pull (or squeeze) the trigger 700 to rotate the trigger 700 in a rotational direction "D" (see FIG. 4A, illustrating clockwise rotational direction "D"), which causes the linking member 900 to pull the first connector 800, thereby causing the first connector 800 to be moved in the direction "E," parallel to the first axis X. This movement, in turn, causes the plunger 300 to be moved from the first position thereof to the second position thereof.

Stated otherwise, the pulling of the trigger 700 causes the fluid-moving assembly 300 to eject the fluid described in this specification toward the predetermined location 110.

The elastic member 950 can bias the trigger 700 to be rotated in the rotational direction "C" when the user releases the trigger 700. The rotation of the trigger 700 in the direction "C" causes the first connector 800 to be moved in the second direction "F," parallel to the first axis X. This, in turn, causes the plunger 330 to be moved from the second position thereof to the first position thereof.

The configuration of the wiping assembly 600 will be described in detail below. As illustrated in FIGS. 4A, 4B, 5 and 6, the wiping assembly 600 may include the shaft 610, a wiping blade 620, an articulating member 630 connecting the shaft 610 and the wiping blade 620 to one another, and at least one elongated track 650.

As illustrated in FIG. 4, the shaft 610 is an elongated structural component that has one end thereof connected to a third portion 816 of the first connector 800 and the opposite end thereof connected to the articulating member 630. The shaft 610 may be, for example, a rod, a bar, etc., made of a material as described in this specification. The shaft 610 is movable between a first position thereof (see FIG. 5), corresponding to the first position of the plunger and a first position of the trigger 700 (e.g., the position of the trigger 700 before being depressed), as shown in FIG. 5, and a second position of the shaft 610 (see FIG. 6), corresponding to the second position of the plunger 330 and a second position of the trigger 700 (when the trigger 700 has been depressed).

The first position of the shaft 610 is a retracted position, in which the articulating member 630 and the wiping blade 620 either do not cover (or overlap) the predetermined location 110, or cover it by a negligible amount such that the field of view of the laparoscope's camera is obstructed only minimally. See FIG. 5, exemplarily illustrating that the articulating member 630 and the wiping blade 620 do not cover the predetermined location 110.

The second position of the shaft 610 is the extended position, in which the wiping blade 620 (and the articulating member 630) has been moved along a length of the at least one elongated track 650 to pass across the entire or virtually the entire length of the predetermined location 110, (see FIG. 6), relative to the position of the wiping blade 620 in the first position of the shaft 610. The wiping blade 620 wipes the predetermined location 110 when being moved from the first position thereof (as illustrated in FIG. 5) to the second position thereof (as illustrated in FIG. 6).

The action of wiping the predetermined location 110 with the wiping blade 620 cleans the predetermined location 110. The wiping action can be performed during a surgical procedure (i.e., with the laparoscope and the apparatus 1000 coupled thereto inserted in a patient's body). The cleaning of the predetermined location 110 by wiping said predetermined location 110 with the wiping blade 620 enables the laparoscope to output a clear image of the surgical site to an external monitor viewable by the surgeon without removing the laparoscope from the patient's body. The cleaning of the predetermined location 110 without removing the apparatus 1000 from the surgical site in the patient's body reduces the length of the surgical procedure. The reduction of surgical time can reduce the patient's recovery time and can increase the availability of medical staff, medical resources and operating rooms in a hospital.

When the trigger 700 is released by a user, the elastic member 950 is configured to rotate the trigger about the rotational direction "C," causing the first connector 800 to move the shaft 610 and the plunger 330 to their respective first positions. The moving of the shaft 610 to the first position thereof, relative to the second position thereof, causes the wiping blade 620 to be moved across the predetermined location 110, thereby wiping the predetermined location 110 clean.

Figure 7:
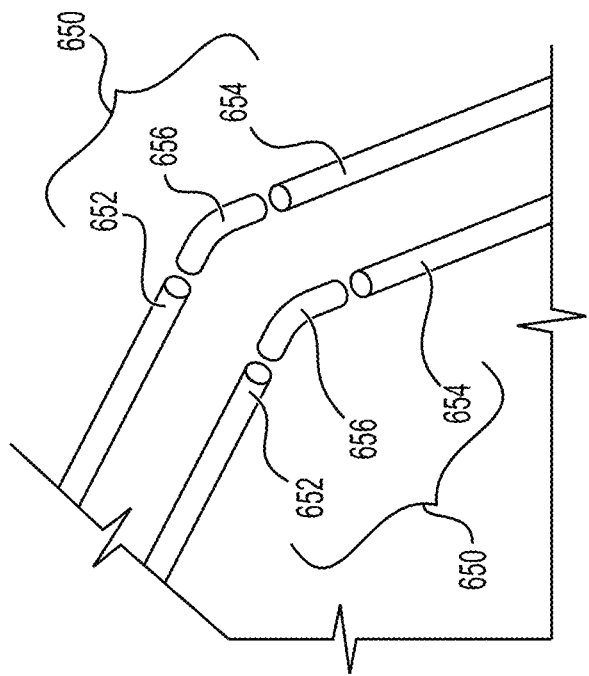
FIG. 7 is an exploded perspective view illustrating a pair of elongated tracks included in the apparatus of FIG. 1 in isolation from the other components of said apparatus.

As illustrated in FIGS. 5-7, the at least one elongated track 650 may include a pair of elongated tracks 650. Each elongated track 650 may include a bend or a curve along its length.

As more clearly illustrated in FIG. 7, each one of the elongated tracks 650 includes a first track portion 652, a second track portion 654, and a bent or curved portion 656 (which may be referred to as the "bent" portion hereinafter for brevity). The bent portion 656 connects the first and second track portions 652, 654 to one another in each of the elongated tracks 650.

As illustrated in FIGS. 5 and 6, each first track portion 652 may extend along the length direction of the body 180 of the second elongated housing component 150. Each second track portion 654 may extend adjacent to the predetermined location 110. Since the first and second track portions 652, 654 of each elongated track 650 extend in different directions, as illustrated in FIGS. 5 and 6, the bent portion 656 of each elongated track 650 connects the first and second track portions 652, 654 of each elongated track 650 along a curved path (or bent path).

As illustrated in FIGS. 5-7, the first track portions 652 of the pair of elongated tracks 650 may be parallel to one another, the second track portions 655 of the pair of elongated tracks 650 may be parallel to one another, and the bent portion 656 of the pair of elongated tracks 650 may be spaced apart from one another by an equal distance along their respective lengths. Stated otherwise, the first and second elongated tracks 650 illustrated in FIGS. 5-7 may be spaced apart from one another by a constant distance along their respective lengths.

Referring to FIGS. 4 and 5, the articulating member 630 may include a plurality of member components 632 consecutively arranged and rotatably coupled to one another. For example, as illustrated in FIGS. 4 and 5, a plurality of hinges 634 or other similar mechanisms can be used to rotatably connect the member components 632 to one another.

A least one of the plurality of member component 632 is movably coupled to the at least one elongated track 650 such that the at least one member component 632 can be moved along the length of the at least one member component 632.

In a non-limiting embodiment, as illustrated in FIGS. 5-6, each one of the plurality of member components 632 may be movably connected to the first elongated track 650 and to the second elongated track 650 such that each said member component 632 can be moved along the first track portion 652, the second track portion 654 and the bent portion 656 of each one of the first and second elongated tracks 650.

A roller mechanism, whereby each end of each member component 632 is connected to a respective one of the first and second elongated tracks 650 via roller, can be employed to enable each member component 632 to be moved (or rolled) along the length of the first elongated track 650 and along the length of the second elongated track 650. The roller mechanism can be configured to enable each end of each member component 632 to be moved along the length of the pair of elongated tracks 650 without being separated, or disconnected, from each track 650.

Other mechanism may be used to movably connect to the member components 632 to the first and second elongated tracks 650. For example, a slidable mechanism, in which a protrusion in a first end of each member component 632 is inserted in a first matching groove extending along the length of the first elongated track 650, and a protrusion in a second end of each member component 632 is inserted in a second matching groove extending along the length of the second elongated track 650, can be employed to enable the protrusions to be moved (or slid) along the length of the first and second elongated tracks 650.

The wiping blade 620 can be movably connected to the first and second tracks 650 in the say way as the member components 632. Therefore, the wiping blade 620 can have the same structural configuration as the member components 632 at portions thereof that connect the wiping blade 620 to the first and second elongated tracks 650.

As illustrated in FIGS. 5 and 6, the wiping blade 620 can be connected to its adjacent member component 632 of the articulating member 630 via at least one hinge 634. This configuration enables the wiping blade 620 to be moved along the first and second elongated tracks 650 by the articulating member 630, which itself is moved by the shaft 610 as described in this specification, to wipe the predetermined location 110 while being moved therealong.

Based on the description of the apparatus 1000 as provided in this specification, it becomes clear that when a user squeezes the trigger 700 (which causes the trigger 700 to be rotated in the rotational direction "D"), the fluid-moving assembly 300 directs (or sprays) fluid from the interior chamber 320 to the predetermined location 110 (by virtue of the first connector 800 moving, or pushing, the plunger 330 from the first position thereof to the second position thereof), and the wiping blade 620 wipes the predetermined location 110 (by virtue of the first connector 800 moving, or pushing, the shaft 610 from the first position thereof to the second position thereof). As indicated above, the wiping blade 620 wipes the predetermined location 110 by being moved across the predetermined location 110 from the first position of the wiping blade 620, illustrated in FIG. 5, to the second position of the wiping blade 620, illustrated in FIG. 6.

The simultaneous spraying/wetting of the predetermined location 110 and wiping the sprayed/wetted predetermined location 110 with the wiping blade 620 cleans the predetermined location well. This is because the wetting process enables the wiping blade 620 to more efficiently remove bodily fluids/matter that may be smeared on the predetermined location 110 during a laparoscopic procedure. The fact that the wetting process and the wiping process can be performed by engaging a single component of the apparatus 1000 (i.e., by pressing the trigger 700), simplifies the operation of the apparatus 1000 during a laparoscopic procedure, and frees up one of the hands of the operating surgeon since the operating surgeon can hold the apparatus 1000 and squeeze the trigger 700 by using one hand. This configuration enables the surgeon to use the surgeon's other hand to perform other tasks during the procedure, resulting in an increased efficiency of time utilization and reducing the total time spent to perform the laparoscopic procedure.

The release of the squeezed trigger 700 enables the elastic member 950 to rotate the trigger 700 from the second position thereof to the first position thereof (i.e., to rotate in the rotational direction "C"). This movement causes the wiping blade 620 to be moved from the second position thereof, as illustrated in FIG. 6, to the first position thereof, as illustrated in FIG. 5. The wiping blade 620 wipes the predetermined location 110 while being moved from the second position thereof to the first position thereof, thereby, increasing the cleaning performance of the apparatus 1000 by wiping off the predetermined location 110 any biological matter that was not removed from the predetermined location 110 when the wiping blade 620 was moved from the first location thereof to the second location thereof.

In addition, the release of the squeezed trigger 700 causes the plunger 330 to be moved back (i.e., to be moved from its second position to its first position). The movement of the plunger 330 from the second position thereof to the first position thereof causes the interior chamber 320 to be refilled with the fluid.

Therefore, it becomes clear that a surgeon or other medical professional can use a single hand to hold and operate the apparatus 1000 of the present disclosure with a laparoscope selectively connected thereto. More specifically, the surgeon or other medical professional can use a single hand to squeeze the trigger 700 to spray and wipe the predetermined location 110 while the laparoscope and the apparatus 1000 are inserted in a patient's body. Due to the configuration of the apparatus 1000, the releasing of the trigger 700 wipes the predetermined location again 110 (after the first wipe that results from squeezing the trigger 700), refills the interior chamber 320 of the of the fluid reservoir 310 with the cleaning fluid, and makes the apparatus 1000 ready to be used again to clean the view of the laparoscope's camera by squeezing the trigger 700.

Figure 8:
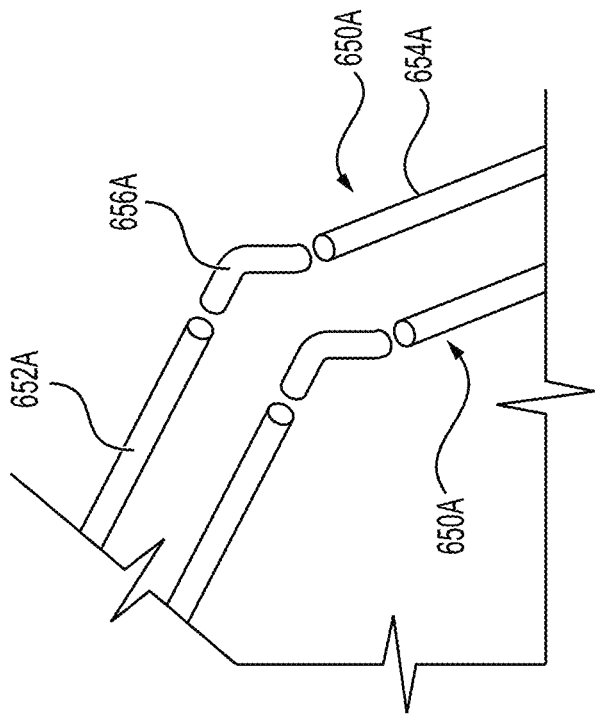
FIG. 8 is an exploded perspective view illustrating a different pair of elongated tracks that can replace the pair of elongated tracks included in the apparatus of FIG. 1.

While the elongated tracks 650 are illustrated as having a curved (or round) portion 656, the present disclosure is not limited to this configuration. For example, as illustrated in FIG. 8, elongated tracks 650A can have an angular portion 656A connecting their respective first and second portions 652A, 654A to one another.

Figure 9:
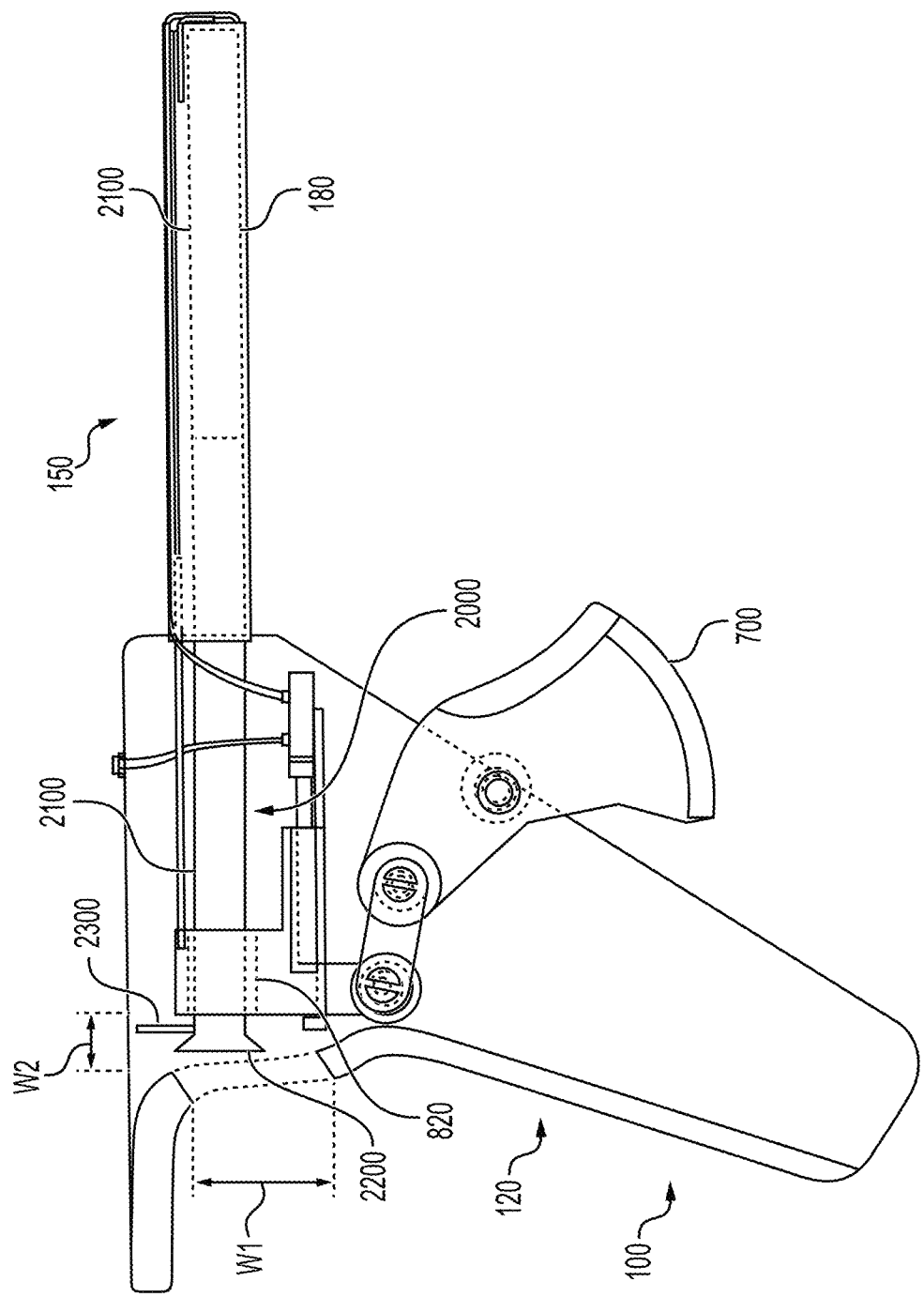
FIG. 9 is a side view illustrating the apparatus of FIG. 1 coupled to an exemplary laparoscope.

FIG. 9 illustrates the apparatus 1000 of FIGS. 1-7 connected to an exemplary laparoscope 2000. As illustrated in FIG. 9, the laparoscope 2000 may include an elongated body 2100, a first protrusion 2200 and a second protrusion 2300. Referring to FIG. 9, a rear portion of the elongated body 2100 of the laparoscope 2000 may be inserted in (and extend through) the interior space 820 of the first connector 800. Referring to FIG. 9, and a front portion of the elongated body 2100 may be inserted in (and extend through) the interior space 194 of the first tubular component 182 of the body 180 of the second elongated housing component 150.

Referring to FIG. 9, the first and/or second handle portions 130, 140 of the first housing component 120 may include a first through opening W1, enabling a first external laparoscopic component to be connected to the first protrusion 2200 of the laparoscope 2000, through the housing 100, when laparoscope 2000 is connected to the apparatus 1000. In addition, and with reference to FIG. 9, the first and/or second handle portions 130, 140 of the first housing component 120 may include a second through opening W2, enabling a second external laparoscopic component to be connected to the second protrusion 2300 of the laparoscope 2000, through the housing 100, when laparoscope 2000 is connected to the apparatus 1000.

A method of operating the apparatus 1000 of the present disclosure includes: obtaining the apparatus 1000, connecting a laparoscope to the obtained apparatus 1000, and moving a trigger 700 of the obtained apparatus 1000 in a first direction to direct a fluid on a camera lens of the laparoscope on or a transparent layer of material covering the lens of the laparoscope (i.e., on the predetermined location 110), and cause a wiping blade 620 of the obtained apparatus 1000 to move in a first direction to wipe the lens or the transparent layer of material covering said lens with said fluid thereon.

The method may also include the step of moving the trigger 700 of the obtained apparatus 1000 in a second direction, opposite to the first direction thereof, to cause the wiping blade 620 to move in a second direction, opposite to said first direction thereof, to wipe said lens or said transparent layer of material covering said lens.

While the present disclosure has been particularly shown and described with reference to exemplary embodiments thereof, it will be apparent to those of ordinary skill in the art that various changes in form and detail may be made therein without departing from the spirit and scope of the present disclosure as defined by the following claims.

What is claimed is:

1. An apparatus for cleaning a laparoscope, comprising:
a housing configured to be selectively connected to the laparoscope, the housing including a first housing component and a second housing component, said second housing component terminating in a first transparent portion thereof configured to cover a camera of the laparoscope and having a first end and a second end;
a fluid-moving assembly connected to the housing, wherein the fluid-moving assembly is configured to receive a fluid for cleaning the laparoscope and to direct the received fluid toward the first transparent portion of the housing;
a wiping assembly connected to the housing, wherein the wiping assembly includes a wiping blade configured to wipe the first transparent portion of the housing; and
a trigger movably connected to the housing, the fluid-moving assembly and the wiping assembly, wherein the trigger is configured to be selectively moved between a first position thereof and a second position thereof,
wherein, when the trigger is moved from the first position thereof to the second position thereof, the fluid-moving assembly is configured to direct the received fluid toward the first transparent portion of the housing and the wiping assembly is configured to move the wiping blade to wipe the first transparent portion of the housing, and wherein the wiping assembly comprises:
a shaft movably connected to the trigger such that, when the trigger is in the first position, the shaft is disposed in a corresponding first position thereof, and when the trigger is moved to the second position, the shaft is moved to a corresponding second position thereof, wherein the movement of the shaft from the first position thereof to the second position thereof is configured to cause the wiping blade to wipe the first transparent portion of the housing;
the wiping blade;
an articulating member connecting the shaft and the wiping blade to one another, wherein a first end of the shaft is connected to the trigger, and a second end of the shaft, opposite to the first end thereof, is connected to the articulating member; and
at least one elongated track having a length extending from said second end of said housing component to said first end of said housing component, wherein the articulating member is movably connected to the at least one elongated track along the length of said at least one elongated track,
wherein the wiping blade is movably connected to the at least one elongated track along the length of said at least one elongated track,
wherein the at least one elongated track has a bent portion or a curved portion along the length thereof,
wherein the at least one elongated track includes a first track portion, a second track portion, and the bent or curved portion thereof connecting the first and second track portions to one another, and
wherein the second track portion is disposed on the first transparent portion of the housing such that the wiping blade can be used to wipe the first transparent portion of the housing when the wiping blade is moved from the first track portion through the bent or curved portion thereof and along the second track portion of the at least one elongated track.

2. The apparatus of claim 1, wherein the fluid-moving assembly comprises:
a fluid reservoir, the fluid reservoir having an interior chamber;
a first conduit in fluid communication with the interior chamber of the fluid reservoir, the first conduit being configured to convey the fluid from an exterior fluid source to the interior chamber such that the fluid can be received in the interior chamber; and
a second conduit in fluid communication with the interior chamber of the fluid reservoir, the second conduit being configured to convey the received fluid out of the interior chamber and toward the first transparent portion of the housing; and
a plunger movably engaged with the interior chamber of the fluid reservoir, wherein the plunger is configured to be moved within the interior chamber of the fluid reservoir between a first position thereof, in which the plunger extends inside of the interior chamber of the fluid reservoir by a first distance, and a second position thereof, in which the plunger extends inside of the interior chamber of the fluid reservoir by a second distance, greater than the first distance, wherein, a movement of the plunger from the first position thereof to the second position thereof is configured to push the fluid received in the interior chamber of the fluid reservoir out of the interior chamber of the fluid reservoir via the second conduit.

3. The apparatus of claim 2, wherein the trigger is movably connected to the plunger such that a selective movement of the trigger from the first position thereof to the second position thereof is configured to move the plunger from the first position of the plunger to the second position of the plunger.

4. The apparatus of claim 3, wherein the trigger is rotatably connected to the housing.

5. The apparatus of claim 1, wherein the articulating member includes a plurality of member components consecutively arranged and rotatably coupled to one another, wherein at least one member component of the plurality of member components is movably coupled to the at least one elongated track such that the at least one member component can be moved along the first track portion, the second track portion, and the bent or curved portion of the at least one elongated track.

6. The apparatus of claim 5, wherein each one of the plurality of member components of the articulating member is movably connected to the at least one elongated track.

7. The apparatus of claim 5, further comprising:
an elongated guide member connected to the housing and extending along a first axis;
a first connector movably connected to the elongated guide member such that the first connector can be selectively moved parallel to the first axis; and
a linking member rotatably coupled to the trigger and rotatably coupled to the first connector;
wherein the fluid-moving assembly comprises:
a fluid reservoir; the fluid reservoir having an interior chamber;
a first conduit in fluid communication with the interior chamber of the fluid reservoir, the first conduit being configured to convey the fluid from an exterior fluid source to the interior chamber such that the fluid can be received in the interior chamber; and
a second conduit in fluid communication with the interior chamber of the fluid reservoir, the second conduit being configured to convey the received fluid out of the interior chamber and toward the first transparent portion of the housing; and
a plunger movably engaged with the interior chamber of the fluid reservoir, wherein the plunger is configured to be moved within the interior chamber of the fluid reservoir between a first position thereof, in which the plunger extends inside of the interior chamber of the fluid reservoir by a first distance, and a second position thereof, in which the plunger extends inside of the interior chamber of the fluid reservoir by a second distance, greater than the first distance, wherein, a movement of the plunger from the first position thereof to the second position thereof is configured to push the fluid received in the interior chamber of the fluid reservoir out of the interior chamber of the fluid reservoir via the second conduit, wherein the first end of the shaft of the wiping assembly is connected to the first connector and the second end of the shaft of the wiping assembly is connected to a first one of the plurality of the member components of the articulating member, and the wiping blade is connected to a second one of the plurality of the member components of the articulating member, and wherein the plunger includes a first end connected to the first connector and a second end, opposite to the first end thereof, engaged with the interior chamber of the fluid reservoir.

8. The apparatus of claim 7, wherein the housing includes a first housing component and a second elongated housing component extending from the first housing component,
wherein the elongated guide member and the trigger are connected to the first housing component,
wherein the second elongated housing component includes the first transparent portion of the housing, and
wherein the second elongated housing component is configured to house therein a portion of the laparoscope that includes the camera thereof.

* * * * *